United States Patent [19]
Dolan et al.

[11] Patent Number: 6,106,864
[45] Date of Patent: Aug. 22, 2000

[54] PHARMACEUTICAL FORMULATIONS CONTAINING DARIFENACIN

[75] Inventors: Thomas Francis Dolan; Michael John Humphrey; Donald John Nichols, all of Sandwich, United Kingdom

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/029,072

[22] PCT Filed: Aug. 21, 1996

[86] PCT No.: PCT/EP96/03719

§ 371 Date: Mar. 15, 1998

§ 102(e) Date: Mar. 15, 1998

[87] PCT Pub. No.: WO97/09980

PCT Pub. Date: Mar. 20, 1997

[30] Foreign Application Priority Data

Sep. 15, 1995 [GB] United Kingdom .................... 9518953

[51] Int. Cl.⁷ .................. A61K 9/14; A61K 31/40
[52] U.S. Cl. .................... 424/488; 514/422; 514/966
[58] Field of Search .............. 424/488; 514/422, 514/966

[56] References Cited

U.S. PATENT DOCUMENTS

5,233,053  8/1993  Cross et al. ............................. 548/568

FOREIGN PATENT DOCUMENTS

0388054  9/1990  European Pat. Off. .
9519164  7/1995  WIPO .

*Primary Examiner*—Kimberly Jordan
*Attorney, Agent, or Firm*—Peter C. Richardson; Gregg C. Benson; James T. Jones

[57] ABSTRACT

There is provided a pharmaceutical dosage form adapted for administration to the gastrointestinal tract of a patient, comprising darifenacin, or a pharmaceutically acceptable salt thereof, and a pharmaceutically acceptable adjuvant, diluent or carrier, characterized in that the dosage form is adapted to deliver at least 10% by weight of the darifenacin, or the pharmaceutically acceptable salt thereof, to the lower gastrointestinal tract of the patient. The formulation minimizes unwanted side-effects and increases the bioavailability of darifenacin.

28 Claims, No Drawings

PHARMACEUTICAL FORMULATIONS CONTAINING DARIFENACIN

This is a National Phase filing under 35 U.S.C. §171 based on PCT/EP96/03719 having an international filing date Aug. 21, 1996.

This invention relates to pharmaceutical dosage forms of darifenacin and its pharmaceutically acceptable salts.

Darifenacin is (S)-2-{1-[2-(2,3-dihydrobenzofuran-5-yl)ethyl]-3-pyrrolidinyl}-2,2-diphenyl-acetamide and is disclosed in European Patent No 0388054, Examples 1B and 8, and is referred to therein as 3-(S)-(−)-(1-carbamoyl-1,1-diphenylmethyl)-1-[2-(2,3-dihydro-benzofuran-5-yl)ethyl]pyrrolidine. It is indicated in the treatment of urinary incontinence and irritable bowel syndrome and has the following structure:

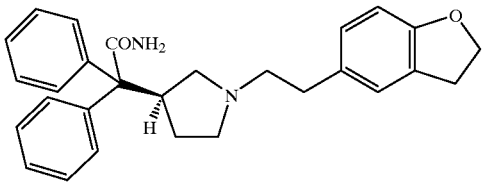

Clinical investigations have shown a major metabolite of darifenacin to be the following 3'-hydroxyl derivative:

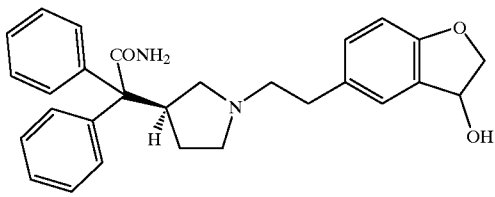

It appears that the metabolite is 6-fold less selective for muscarinic M3 receptors over M1 receptors in comparison with darifenacin, and so the metabolite is more likely than darifenacin to produce unwanted side-effects such as dry mouth, confusion and blurred vision.

It has now been found that delivering darifenacin and its pharmaceutically acceptable salts to the lower gastrointestinal tract (e.g. in a sustained release formulation) gives rise to a greater ratio of darifenacin to metabolite in the systemic circulation. This increases the bioavailability of darifenacin, which is likely to minimize any unwanted side-effects. This is surprising because a slower release rate normally leads to a slower delivery to liver enzymes and a greater degree of metabolism of an administered drug.

Thus, according to the present invention, there is provided a pharmaceutical dosage form adapted for administration to the gastrointestinal tract of a patient, comprising darifenacin, or a pharmaceutically acceptable salt thereof, and a pharmaceutically acceptable adjuvant, diluent or carrier; characterized in that the dosage form is adapted to deliver at least 10% by weight of the darifenacin, or the pharmaceutically acceptable salt thereof, to the lower gastrointestinal tract of the patient.

The dosage forms of the invention may be of the sustained or delayed release type, and so release the darifenacin, or the pharmaceutically acceptable salt thereof, to the gastrointestinal tract of the patient over or after a sustained period of time following administration of the dosage form to the patient. However, when the dosage forms are administered rectally, conventional rectal formulations may be used.

By "lower gastrointestinal tract" is meant the portion of the gastrointestinal tract between the region of the ileocaecal junction and the rectum inclusive.

"Patient" means primarily a human patient, although the formulations of the present invention may be useful in the treatment of non-human animals.

Preferably, the dosage forms of the invention are adapted to deliver at least 25%, and more preferably 50% by weight of the darifenacin, or the pharmaceutically acceptable salt thereof, to the lower gastrointestinal tract.

Preferably, no more than 90% by weight of the darifenacin, or the pharmaceutically acceptable salt thereof, is released 4 hours after dosing; more preferably no more than 90% by weight of the darifenacin, or the pharmaceutically acceptable salt thereof, is released 8 hours after dosing; and most preferably, no more than 90% by weight of the darifenacin, or the pharmaceutically acceptable salt thereof, is released 16 hours after dosing.

The conditions in the gastrointestinal tract are thought to be reproduced in vitro using Apparatus 1 described in USP XXII at page 1578, having baskets of 40 mesh (381 μm apertures), a rotation speed of 100 rpm and a dissolution medium of water at 37° C. Therefore, the sustained release formulations of the invention may be defined alternatively as a pharmaceutical dosage form adapted for administration to the gastrointestinal tract of a patient, comprising darifenacin, or a pharmaceutically acceptable salt thereof, and a pharmaceutically acceptable adjuvant, diluent or carrier; characterized in that the dosage form is adapted to release the darifenacin, or the pharmaceutically acceptable salt thereof, in Apparatus 1 described in USP XXII at page 1578, having baskets of 40 mesh (381 μm apertures), a rotation speed of 100 rpm and a dissolution medium of water at 37° C., over a sustained period of time.

Particular oral dosage forms include:

(a) those in which the darifenacin, or the pharmaceutically acceptable salt thereof, is embedded in a matrix from which it is released by diffusion or erosion;

(b) those in which the darifenacin, or the pharmaceutically acceptable salt thereof, is present in a multiparticulate core;

(c) those in which there is an impermeable coating provided with an aperture through which the darifenacin, or the pharmaceutically acceptable salt thereof, is released;

(d) those in which there is a coating of low aqueous solubility;

(e) those in which there is a semipermeable coating;

(f) those in which the darifenacin is present as an ion exchange resin complex; and (g) pulsatile devices from which the darifenacin is released at specific points in the gastrointestinal tract.

It will be apparent to those skilled in the art that some of the above means of achieving sustained release may be combined: for example a matrix containing the active compound may be formed into a multiparticulate and/or coated with an impermeable coating provided with an aperture.

Dealing with each category in turn:

(a) In matrix systems, which are preferred, the active compound is embedded or dispersed in a matrix of another material which serves to retard the release of the active compound into an aqueous environment. Suitable matrix materials include hydroxypropyl methylcellulose and hydroxypropyl cellulose. Matrix formulations according to the present invention preferably comprise high molecular weight (i.e. 85,000–95,000 mass units) hydroxypropyl methylcellulose.

(b) In multiparticulate cores, the active compound is present in a number of particles which also contain adjuvants, diluents or carriers. Suitable adjuvants, diluents and carriers include microcrystalline cellulose (preferably having a particle size of 50 μm) and lactose (preferably having a particle size equivalent to 110 mesh (137.5 μm apertures)).

Typically, the blended ingredients are formed into a wet mass which is extruded and spheronized to form beads which are then dried.

(c) Impermeable coatings are applied to tablets containing the active compound. "Impermeable" means that no significant transport of the active compound can take place across the coating during the intended release period of the formulation. Suitable materials include film-forming polymers and waxes [e.g. thermoplastic polymers such as poly(ethylene-covinyl acetate), poly (vinyl chloride), ethyl cellulose and cellulose acetate] and the coating thickness is preferably greater than 100 μm. The aperture may be formed by drilling, or if the coated formulation is conical, by cutting off the tip.

(d) Coatings of low aqueous solubility include polymers. The solubility of such polymers may be pH-dependent, for example substantially insoluble at pH<5 (so that dissolution does not take part in the stomach) and water soluble at pH>5. Preferred pH-sensitive polymers include shellac, phthalate derivatives (including cellulose acetate phthalate, polyvinylacetate phthalate), polyacrylic acid derivatives, and vinyl acetate and crotonic acid copolymers.

(e) Semipermeable membrane coatings allow the active compound to diffuse across the membrane or through liquid filled pores within the membrane. Suitable coating materials include polymers such as cellulose ester or ether, and acrylic polymers. Preferred materials include ethyl cellulose, cellulose acetate and cellulose acetate butyrate.

(f) Darifenacin resinates may be prepared by treating anionic ion exchange resin beads (for example sodium polystyrene sulphonate) with an acid addition salt of darifenacin.

(g) Pulsatile devices have the capacity to release drug at various points of the gastrointestinal tract. They may depend on osmotic potential to trigger release (see U.S. Pat. No. 3,952,741) or erosion of polymeric material due to changes in pH or microbial degradation. Suitable polymeric materials include pectin [Rubinstein et al, 1991, Pectic salt as a colonic delivery system, Proceed. Intern. Symp. Control. Rel. Bioact. Mater.], methacrylate-galactomannan [Lehman et al, 1991, Methacrylate-galactomannan coating for colonic specific drug delivery, ibid], matter containing azobonds [Kopeckova et al, 1991, Bioadhesive polymers for colon specific drug delivery, ibid], chondroitin [Sintov et al, 1991, Colonic administration of indomethacin using modified chondroitin in a cannulated dog model, ibid], dextran hydrogels [Bronsted et al, 1993, A novel hydrogel system designed for controlled drug delivery to the colon, ibid], methacrylic acid copolymers [Siefke et al, 1993, β-Cyclodextrin matrix films for colon specific drug delivery, ibid], and amylose [Milojevik et al, In vitro and in vivo evaluation of amylose coated pellets for colon specific drug delivery, ibid]. Delivery to specific points of the gastrointestinal tract may also be achieved using multilayered tablets [Gazzaniga et al, 1993, Time dependent oral delivery system for colon specific release, ibid], or hydrogel plugs in a capsule [Binns et al, Application of a pH-independent PEG-based hydrogel to afford pulsatile drug delivery].

Preferably, in the dosage forms of the present invention, the darifenacin is in the form of its hydrobromide salt (except when the darifenacin is present as an ion exchange resin complex).

A preferred oral formulation is a tablet consisting essentially of darifenacin hydrobromide in a high molecular weight hydroxypropyl methylcellulose matrix together with anhydrous dibasic calcium phosphate and magnesium stearate. The tablet may be colour coated by conventional methods. Preferably, hydroxypropyl methylcellulose makes up 56–58% w/w of the tablet, magnesium stearate makes up approximately 1% of the tablet, and darifenacin hydrobromide and anhydrous dibasic calcium phosphate make up the balance. The darifenacin hydrobromide content may range from 4 mg–54 mg per tablet, depending on the dose to be delivered. Such tablets would be suitable for administration once daily.

Preferably, the dosage forms of the present invention are adapted for oral administration, but they may also be adpated for rectal administration. Rectal suppository formulations may be prepared by dispersing the active ingredient in hardened oils or waxes using conventional methods.

According to another aspect of the invention, there is provided a method of treatment of irritable bowel syndrome or urinary incontinence, which comprises delivering darifenacin, or a pharmaceutically acceptable salt thereof, to the lower gastrointestinal tract of a patient in need of such treatment. The method may be performed by administering a dosage form of the invention to the gastrointestinal tract of a patient in need of such treatment.

The invention is illustrated by the following examples in which the following materials are used:

Methocel™ K4M—a high molecular weight hydroxypropyl methylcellulose with a number average in molecular weight of 89,000. It is classified in the USP as 2208 and a 2% solution in water has a nominal viscosity of 4000 cps. It has a methoxy content of 19–24% and a hydroxypropoxy content of 7–12%;

Methocel™ E4M—a high molecular weight hydroxypropyl methylcellulose with a number average molecular weight of 93,000. It is classified in the USP as 2910 and a 2% solution in water has a nominal viscosity of 4000 cps. It has a methoxy content of 28–30% and a hydroxypropoxy content of 7–12%;

Methocel™ K100LV—a low molecular weight hydroxypropyl methylcellulose. It is classified in the USP as 2208 and a 2% solution in water has a nominal viscosity of 100 cps. It has a methoxy content of 19–24% and a hydroxypropoxy content of 7–12%;

Klucel EF™—hydroxy propyl cellulose with a number average molecular weight of 60,000;

Ethocel™—ethyl cellulose;

Avicel™ PH101—microcrystalline cellulose with an average particle size of 50 μm;

Lactose regular—lactose with a particle size equivalent to 110 mesh (137.5 μm apertures);

Lactose Fast Flo™—spray dried lactose; and

EmcomPress™—dibasic calcium phosphate (anhydrous).

Aerosil 200—colloidal anhydrous silica

EXAMPLE 1 (COMPARATIVE)

Fast release matrix tablet

| Ingredient | Specification | mg/unit theory | g/batch (actual) |
|---|---|---|---|
| Darifenacin hydrobromide | Pfizer | 23.810 | 30.19 |
| Methocel K4M | Ph Eur | 12.000 | 15.00 |
| Methocel K100LV Premium | USP | 28.000 | 35.00 |
| Fast flo Lactose | Ph Eur | 134.190 | 167.70 |
| Magnesium Stearate | Ph Eur | 2.000 | 2.50 |
| TOTAL | | 200.000mg | |

The Methocel K4M, K100LV premium, darifenacin and Fast-flo lactose were blended in a Turbula blender for 10 minutes. The mixture was then screened using a 30 mesh (500 μm apertures) screen and reblended for a further 10 minutes. Magnesium stearate was screened through a 30 mesh (500 μm apertures) screen and added to the mixture before blending for a further 5 minutes. The blend was then subjected to compression on a tabletting machine using 8 mm round normal convex tooling to make 1250 tablets.

EXAMPLE 2

Medium release matrix tablet

| Ingredient | Specification | mg/unit (theory) | g/batch (actual) |
|---|---|---|---|
| Darifenacin hydrobromide | Pfizer | 23.810 | 30.19 |
| Methocel K4M | Ph Eur | 30.000 | 37.50 |
| Methocel E4M | Ph Eur | 30.000 | 37.50 |
| Fast flo Lactose | Ph Eur | 114.190 | 142.70 |
| Magnesium Stearate | Ph Eur | 2.000 | 2.50 |
| TOTAL | | 200.000mg | |

The Methocel K4M, darifenacin and Fast-flo lactose were blended in a suitable blender for 10 minutes. The mixture was then screened using a 30 mesh (500 μm apertures) screen and reblended for a further 10 minutes. Magnesium stearate was screened through a 30 mesh (500 μm apertures) screen and added to the mixture before blending for a further 5 minutes. The blend was then subjected to compression on a tabletting machine using 8 mm round normal convex tooling to make 1250 tablets.

EXAMPLE 3

Slow release matrix tablet

| Ingredient | Specification | mg/unit (theory) | g/batch (actual) |
|---|---|---|---|
| Darifenacin hydrobromide | Pfizer | 23.810 | 30.19 |
| Anhydrous dibasic calcium phosphate | USP | 59.790 | 74.70 |
| Methocel K4M | Ph Eur | 114.400 | 143.00 |
| Magnesium Stearate | Ph Eur | 2.000 | 2.50 |
| TOTAL | | 200.000 | |

The Methocel K4M, darifenacin and anhydrous dibasic calcium phosphate were blended in a Turbula blender for 10 minutes. The mixture was then screened using a 30 mesh (500 μm apertures) screen and reblended for a further 10 minutes. Magnesium stearate was screened through a 30 mesh (500 μm apertures) screen and added to the mixture before blending for a further 5 minutes. The blend was then subjected to compression on a tabletting machine using 8 mm round normal convex tooling to make 1250 tablets.

EXAMPLE 4

Encapsulated coated core multiparticulates (a) Preparation of Uncoated Cores

| Ingredient | Specification | g/kg (theory) | g/batch (actual) |
|---|---|---|---|
| Darifenacin hydrobromide | Pfizer | 119.048 | 119.76 |
| Avicel PH101 | Ph Eur | 359.499 | 359.50 |
| Lactose Regular | Ph Eur | 359.499 | 359.50 |
| Fumaric acid | NF | 161.954 | 161.95 |
| Purified water | Ph Eur | (500.000) | 500.0 |
| TOTAL | | 1000.000 g | 1000.71 |

The Avicel PH101, lactose regular, darifenacin and fumaric acid were blended in an Apex 2L Y cone for 10 minutes. The mixture was then screened using a 30 mesh (500 μm apertures) screen and re-blended for 10 minutes. Purified water was added to form a wet mass amenable to extrusion. The resultant wet mass was extruded using an Nica E 140 extruder (1 mm screen) and then spheronised using a Caleva spheroniser to form multiparticulate beads. The beads were then dried using a bed temperature of 50° C. for 1 hour to remove excess moisture.

(b) Preparation of Final Formulation

| Ingredient | Specification | mg/unit (theory) | g/batch (actual) |
|---|---|---|---|
| Darifenacin uncoated cores | Pfizer | 200.000 | 150.30 |
| Ethyl cellulose N-10 | NF | 17.750 | 13.32 |
| Klucel EF | NF | 7.250 | 5.44 |
| Ethyl Acetate | NF | 237.500 | 178.2 |
| Isopropyl alcohol | NF | 237.500 | 178.1 |
| TOTAL | | 225.000 | |

Filled into white size 2 gelatine capsule shells.

Ethyl acetate and isopropyl alcohol were stirred in a suitable vessel to ensure thorough mixing. To this mixture the Klucel EF and ethyl cellulose N10 were added and the solution stirred until complete dissolution had taken place. The uncoated beads were added to a fluidised bed coater and using an inlet temperature of 40° C. the beads were coated with the solution containing the Klucel EF and ethylcellulose N10. On completion of coating the beads were dried for 10 minutes using a bed temperature of approximately 50° C. The coated beads were filled into capsule shells prior to administration.

EXAMPLE 5

Ion exchange resin formulation

| Ingredient | g/batch |
| --- | --- |
| Darifenacin hydrobromide | 60.39 |
| Sodium polystyrene sulphonate | 187.00 |
| Disodium edetate, dihydrate | 1.53 |
| Water | 2000.00 |

The disodium edetate and sodium polystyrene sulphonate were suspended in water. This suspension was then heated to 50° C. whilst stirring. The darifenacin hydrobromide was then added to the suspension and the suspension stirred for a further 2 hours at 50° C. The darifenacin polystyrene sulphonate was then filtered off and washed until free of bromide ions. The darifenacin resinate was then dried under vacuum at 25° C. for approximately 16 hours.

EXAMPLE 6 (COMPARATIVE)

Immediate Release Capsule 7.5 mg

| Ingredient | Specification | mg/unit theory | g/batch (actual) |
| --- | --- | --- | --- |
| Darifenacin hydrobromide | Pfizer | 8.929 | 547.46 |
| Lactose | Ph Eur | 104.453 | 6267.20 |
| Maize starch | Ph Eur | 34.818 | 2089.10 |
| Aerosil 200 | Ph Eur | 0.300 | 18.00 |
| Magnesium stearate | Ph Eur | 1.500 | 84.88 |
| TOTAL | | 150.000 | |

1467.2 g of the lactose was added to all of the darifenacin hydrobromide and blended in an Apex 8L double cone tumbling blender for 20 minutes. This was then milled using a Fitzmill (hammers forward, high speed) through a 1 mm screen and the mill washed with the remaining lactose (4800.0 g). This lactose, Aerosil 200 and maize starch were then added to the darifenacin hydrobromide/lactose preblend prepared initially and blended for 20 minutes in a Gardner 28L double cone tumbling blender. This blend was then passed through a 1 mm screen using a Fitzmill (knives forward, slow speed) and then blended for a further 20 minutes using the 28L blender. Magnesium stearate (88.88 g) was then added and blending continued using the 28L blender for 5 minutes. The final blend was then encapsulated into size 2 hard gelatin capsule shells using a Zanasi capsule filling machine.

EXAMPLE 7

Measurement of in vitro release rates

Dissolution Methods

Dissolution of the formulations of Examples 1–4 was performed using a rotating basket apparatus (Apparatus 1, USPXXII, p. 1578). The formulations were placed in baskets (40 mesh, 381 μm apertures) using a rotation speed of 100 rpm in 900 ml water at 37° C. ±0.5° C. At specified time intervals, 10 ml aliquots were removed from the dissolution vessel from a zone midway between the surface of the dissolution medium and the top of the basket not less than 1 cm from the vessel wall. The first 7 ml is discarded and the remaining solution transferred to an HPLC vial for subsequent analysis.

The release of darifenacin from the formulation of Example 5 was determined according to USP XXIII Apparatus 4 (page 1794). Using a flow rate of 250 ml/hour solutions at 37° C. of the following pH were used to assess release:

0–1 hr pH 1.5; 1–2 hr pH 2.5; 2–3.5 hr pH 4.5; 3.5 hr pH 6.9; 5–24 hr pH 7.2.

Dissolution of the formulation of Example 6 was performed using a rotating basket apparatus (Apparatus 1, USPXXII, p 1578). The formulations were placed in baskets (40 mesh, 381 μm apertures) using a rotation speed of 100 rpm in 900 ml water at 37° C. ±0.5° C. At specified time intervals a 20 ml aliquot of dissolution media was removed from a zone midway between the surface of the dissolution media and the top of the basket not less than 1 cm from the vessel wall. The aliquots were filtered (0.45 μm, Acrodisc) and the first 5 ml of filtrate discarded. 5 ml of the remaining filtrate was then diluted to 25 ml using a 1:1 (v/v) solution of water/methanol prior to analysis by HPLC.

Analysis

For the formulations of Examples 1–5, High Performance Liquid Chromatography (HPLC) was performed using a BDS Hypersil C18 column. The mobile phase used was an aqueous 0.03 M potassium dihydrogen orthophosphate at pH 3.5/methanol, (1000:800 v/v) using a flow rate of 1.5 ml/min at 37° C. and a sample size of 20 μL. Detection was by fluorescence operating at an excitation wavelength of 288 nm (slit width 18 nm) and an mission wavelength of 320 nm (slit width 18 nm).

For the formulation of Example 6, High Performance Liquid Chromatography (HPLC) was performed using a Novapack C18 column. The mobile phase was aqueous 0.01 M sodium acetate containing 0.2% v/v triethylamine at pH 6.0/methanol/acetonitrile (45:54:1, v/v/v) using a flow rate of 1.0 ml/min and a sample size of 50 μ. Detection was by ultraviolet spectroscopy at 230 nm.

Results

EXAMPLE 1 FORMULATION (COMPARATIVE)

| Time (h) | % release (range) |
| --- | --- |
| 1 | 65 (52–81) |
| 2 | 80 (72–92) |
| 4 | 91 (87–96) |

EXAMPLE 2 FORMULATION

| Time (h) | % release |
| --- | --- |
| 1 | 41 (38–46) |
| 4 | 77 (73–81) |
| 8 | 95 (94–96) |

EXAMPLE 3 FORMULATION

| Time (h) | % release |
| --- | --- |
| 1 | 6 (5–7) |
| 8 | 42 (36–44) |

-continued

| Time (h) | % release |
|---|---|
| 16 | 67 (59–70) |

EXAMPLE 4 FORMULATION

| Time (h) | % release |
|---|---|
| 1 | 11 (9–15) |
| 4 | 58 (50–70) |
| 8 | 98 (95–103) |

EXAMPLE 5 FORMULATION

| Time (h) | % release |
|---|---|
| 1 | 11 (10–12) |
| 2 | 25 (24–27) |
| 6 | 55 (51–59) |
| 12 | 79 (77–82) |
| 18 | 90 (89–91) |
| 24 | 94 (93–95) |

EXAMPLE 6 FORMULATION (COMPARATIVE)

| Time (h) | % release |
|---|---|
| 0.25 | 94 |
| 0.5 | 99 |
| 0.75 | 98 |

EXAMPLE 8

Clinical Pharmacokinetics Study

A four way, multiple dose crossover study to investigate the bioavailability of darifenacin and its 3'-hydroxy metabolite when given as a sustained release formulation compared with an immediate release formulation was carried out. Thirteen normal males received the formulations of Examples 1–3 od each for 6 days as well as the formulation of Example 6 three times a day. Plasma samples for drug and metabolite assay were taken over 24 hours on the last day of dosing for each period of the study. The pharmacokinetic parameters (area under the concentration-time curve over 24 hours, AUC, maximum concentration and concentration at 24 hours post dose) were obtained for both drug and metabolite. The table below shows the ratio of AUC values for darifenacin and metabolite ($AUC_{darifenacin}:AUC_{metabolite}$) and the relative bioavailability of darifenacin ($F_{rel\ darifenacin}$) and metabolite ($F_{rel\ metabolite}$) for the formulations versus an immediate release capsule.

Ratio of AUC of darifenacin: metabolite and relative bioavailability ($F_{rel}$) versus an immediate release capsule

| Formulation: | Example 6 (immediate release) | Example 1 | Example 2 | Example 3 |
|---|---|---|---|---|
| Ratio of $AUC_{dar}/AUC_{met}$ | 0.66 | 0.58 | 0.82 | 1.03 |
| $F_{rel\ darifenacin}$ | na | 0.88 | 1.10 | 1.17 |
| $F_{rel\ metabolite}$ | na | 0.98 | 0.82 | 0.70 | na = Not applicable

These data indicate that the relative bioavailability of darifenacin over the metabolite is increased when darifenacin is administered in a sustained release formulation according to the invention.

We claim:

1. A pharmaceutical dosage form adapted for administration to the gastrointestinal tract of a patient, comprising darifenacin, or a pharmaceutically acceptable salt thereof, and a pharmaceutically acceptable adjuvant, diluent, or carrier; characterized in that the dosage form is adapted to release in the lower gastrointestinal tract at least 10% by weight of the darifenacin, or the pharmaceutically acceptable salt thereof.

2. A dosage form as claimed in claim 1, which is adapted to release at least 50% by weight of the darifenacin, or the pharmaceutically acceptable salt thereof, to the lower gastrointestinal tract.

3. A dosage form as claimed in claim 1, which is adapted to release the darifenacin, or the pharmaceutically acceptable salt thereof, to the gastrointestinal tract of the patient over or after a sustained period of time following administration of the dosage form to the patient.

4. A dosage form as claimed in claim 3, wherein no more than 90% by weight of the darifenacin, or the pharmaceutically acceptable salt thereof, is released 4 hours after dosing.

5. A dosage form as claimed in claim 4, wherein no more than 90% by weight of the darifenacin, or the pharmaceutically acceptable salt thereof, is released 8 hours after dosing.

6. A dosage form as claimed in claim 5, wherein no more than 90% by weight of the darifenacin, or the pharmaceutically acceptable salt thereof, is released 16 hours after dosing.

7. A dosage form as claimed in claim 1, wherein the darifenacin is in the form of its hydrobromide salt.

8. A dosage form as claimed in claim 1, which is adapted for oral administration.

9. A dosage form as claimed in claim 1, wherein the darifenacin, or the pharmaceutically acceptable salt thereof, is embedded in a matrix from which it is released by diffusion.

10. A dosage form as claimed in claim 9, wherein the matrix material is high molecular weight hydroxypropyl methylcellulose.

11. A dosage form as claimed in claim 1, which is adapted for rectal administration.

12. A dosage form as claimed in claim 11, which is a suppository.

13. A dosage form as claimed in claim 1, which is adapted to release at least 25% by weight of the darifenacin, or the pharmaceutically acceptable salt thereof, to the lower gastrointestinal tract.

14. A dosage form as defined in claim 1, comprising darifenacin hydrobromide, anhydrous dibasic calcium phosphate, hydroxypropyl methylcellulose, and magnesium stearate.

15. A dosage form as defined in claim 14, wherein said hydroxypropyl methycellulose has a number average molecular weight of 89,000, a methoxy content of 19–24%, and a hydroxypropoxy content of 7–12%.

16. A pharmaceutical dosage form adapted for administration to the gastrointestinal tract of a patient, comprising darifenacin, or a pharmaceutically acceptable salt thereof, and a pharmaceutically acceptable adjuvant, diluent or carrier; characterized in that the dosage form is adapted to release the darifenacin, or the pharmaceutically acceptable salt thereof, in Apparatus 1 described in USP XXII at page 1578, having baskets of 40 mesh (381 µm apertures), a rotation speed of 100 rpm and a dissolution medium of water 37° C., over a sustained period of time.

17. A dosage form as claimed in claim 16, wherein no more than 90% by weight of the darifenacin, or the pharmaceutically acceptable salt thereof, is released after 4 hours.

18. A dosage form as claimed in claim 16, wherein no more than 90% by weight of the darifenacin, or the pharmaceutically acceptable salt thereof, is released after 8 hours.

19. A dosage form as claimed in claim 16, wherein no more than 90% by weight of the darifenacin, or the pharmaceutically acceptable salt thereof, is released after 16 hours.

20. A dosage form as claimed in claim 16, wherein the darifenacin is in the form of its hydrobromide salt.

21. A dosage form as claimed in claim 16, which is adapted for oral administration.

22. A dosage form as claimed in claim 16, wherein the darifenacin, or the pharmaceutically acceptable salt thereof, is embedded in a matrix from which it is released by diffusion.

23. A dosage form as claimed in claim 22, wherein the matrix material is high molecular weight hydroxypropyl methylcellulose.

24. A dosage form as claimed in claim 16, which is adapted for rectal administration.

25. A dosage form as claimed in claim 24, which is a suppository.

26. A method of treatment of irritable bowel syndrome or urinary incontinence, which comprises administering darifenacin, or a pharmaceutically acceptable salt thereof, to the lower gastrointestinal tract of a patient in need of such treatment.

27. A method as claimed in claim 26, which comprises administering a dosage form as defined in claim 1 to the gastrointestinal tract of a patient in need of such treatment.

28. A method as claimed in claim 26, which comprises administering a dosage form as defined in claim 16 to the gastrointestinal tract of a patient in need of such treatment.

* * * * *